United States Patent
Hsieh et al.

(10) Patent No.: US 8,315,353 B1
(45) Date of Patent: Nov. 20, 2012

(54) SYSTEM AND METHOD OF PRIOR IMAGE CONSTRAINED IMAGE RECONSTRUCTION USING SHORT SCAN IMAGE DATA AND OBJECTIVE FUNCTION MINIMIZATION

(75) Inventors: Jiang Hsieh, Brookfield, WI (US); Guang-Hong Chen, Madison, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/493,051

(22) Filed: Jun. 11, 2012
(Under 37 CFR 1.47)

Related U.S. Application Data

(63) Continuation of application No. 12/950,510, filed on Nov. 19, 2010, now Pat. No. 8,204,172, which is a continuation of application No. 12/775,968, filed on May 7, 2010, now abandoned.

(60) Provisional application No. 61/314,937, filed on Mar. 17, 2010.

(51) Int. Cl.
*A61B 6/00* (2006.01)
*G06K 9/00* (2006.01)
(52) U.S. Cl. .................. 378/8; 378/4; 382/131
(58) Field of Classification Search .................. 378/4, 8; 382/131
See application file for complete search history.

(56) References Cited

U.S. PATENT DOCUMENTS

| | | | |
|---|---|---|---|
| 5,860,927 A | 1/1999 | Sakaguchi et al. | |
| 6,487,435 B2 | 11/2002 | Mistretta et al. | |
| 6,614,874 B2 | 9/2003 | Avinash | |
| 6,661,873 B2 | 12/2003 | Jabri et al. | |
| 6,792,072 B2 | 9/2004 | Avinash | |
| 6,841,998 B1 | 1/2005 | Griswold | |
| 6,934,357 B2 | 8/2005 | Boyd et al. | |
| 6,937,690 B2 | 8/2005 | Bruder et al. | |
| 6,950,689 B1 | 9/2005 | Willis et al. | |
| 7,068,826 B2 | 6/2006 | Jabri et al. | |
| 7,203,272 B2 | 4/2007 | Chen | |
| 7,209,535 B2 | 4/2007 | Chen et al. | |
| 7,218,702 B2 | 5/2007 | Mistretta et al. | |
| 7,221,728 B2 | 5/2007 | Edic et al. | |
| 7,289,049 B1 | 10/2007 | Fudge et al. | |
| 7,330,027 B2 | 2/2008 | Kozerke et al. | |

(Continued)

OTHER PUBLICATIONS

Chen et al., "Prior image constrained compressed sensing (PICCS): A method to accurately reconstruct dynamic CT images from highly undersampled projection data sets," Medical Physics Author Manuscript, pp. 1-8, Published in final edited form as: Medical Physics, vol. 35, No. 2, Feb. 2008, pp. 660-663.

(Continued)

*Primary Examiner* — Alexander H Taningco
(74) *Attorney, Agent, or Firm* — Ziolkowski Patent Solutions Group, SC

(57) ABSTRACT

A computerized tomographic system configured to acquire short scan data of an object within a single revolution of a detector array about the object over a first angular range of rotation of the detector array about the object, define a temporal subset of the acquired short scan data over a second angular range of rotation of the detector that is less than the first angular range of rotation, generate a mathematical function that is based on the acquired short scan data and the defined temporal subset of data, minimize the mathematical function, and generate an image of the object using the minimized mathematical function and the data acquired over the second angular range of rotation of the detector.

31 Claims, 11 Drawing Sheets

U.S. PATENT DOCUMENTS

| | | |
|---|---|---|
| 7,358,730 B2 | 4/2008 | Mistretta et al. |
| 7,408,347 B2 | 8/2008 | Mistretta et al. |
| 7,519,412 B2 | 4/2009 | Mistretta |
| 7,545,901 B2 | 6/2009 | Mistretta |
| 7,558,414 B2 | 7/2009 | Griswold |
| 7,613,275 B2 * | 11/2009 | Li et al. ............................ 378/8 |
| 7,647,088 B2 | 1/2010 | Mistretta et al. |
| 7,711,166 B2 | 5/2010 | Mistretta et al. |
| 7,792,347 B2 * | 9/2010 | Manzke et al. ............... 382/131 |
| 8,131,043 B2 * | 3/2012 | Binkley et al. ............... 382/131 |
| 2002/0034276 A1 | 3/2002 | Hu et al. |
| 2004/0136490 A1 | 7/2004 | Edic et al. |
| 2006/0029279 A1 | 2/2006 | Donoho |
| 2006/0045235 A1 | 3/2006 | Bruder et al. |
| 2006/0257012 A1 | 11/2006 | Kaufman et al. |
| 2007/0010731 A1 | 1/2007 | Mistretta |
| 2007/0038073 A1 | 2/2007 | Mistretta |
| 2007/0049817 A1 | 3/2007 | Preiss et al. |
| 2007/0106149 A1 | 5/2007 | Mistretta |
| 2007/0147577 A1 | 6/2007 | Seto |
| 2007/0156044 A1 | 7/2007 | Mistretta et al. |
| 2007/0167707 A1 | 7/2007 | Mistretta et al. |
| 2007/0167728 A1 | 7/2007 | Mistretta et al. |
| 2007/0167729 A1 | 7/2007 | Mistretta et al. |
| 2008/0170654 A1 | 7/2008 | Tkaczyk et al. |
| 2008/0199063 A1 | 8/2008 | O'Halloran et al. |
| 2008/0219535 A1 | 9/2008 | Mistretta et al. |
| 2009/0016932 A1 | 1/2009 | Curcio et al. |
| 2009/0076369 A1 | 3/2009 | Mistretta |
| 2009/0129651 A1 | 5/2009 | Zagzebski et al. |
| 2009/0161932 A1 | 6/2009 | Chen |
| 2009/0161933 A1 | 6/2009 | Chen |
| 2009/0175523 A1 | 7/2009 | Chen et al. |
| 2009/0274355 A1 | 11/2009 | Chen et al. |
| 2010/0128958 A1 | 5/2010 | Chen et al. |
| 2010/0310144 A1 | 12/2010 | Chen et al. |

OTHER PUBLICATIONS

Chen et al., "Temporal resolution improvement using PICCS in MDCT cardiac imaging," Medical Physics, vol. 36, No. 6, Jun. 2009, pp. 2130-2135.

Chen et al., "Prior image constrained compressed sensing (PICSS)," Proc Soc Photo Opt Instrum Eng. Author Manuscript, pp. 1-34, Published in final edited form as: Proc Soc Photo Opt Instrum Eng., Mar. 3, 2008; 6856: 685618. doi:10.1117/12.770532.

Nett et al., "Tomosynthesis via Total Variation Minimization Reconstruction and Prior Image Constrained Compressed Sensing (PICSS) on a C-arm System," Proc Soc Photo Opt Instrum Eng. Author Manuscript, pp. 1-14, Published in final edited form as: Proc Soc Photo Opt Instrum Eng., Mar. 18, 2008; 6913: nihpa92672. doi:10.1117/12.771294.

Fessler et al., "Iterative Image Reconstruction in MRI With Separate Magnitude and Phase Regularization," pp. 1-4, 2004.

Lustig et al., "Rapid MR Imaging with 'Compressed Sensing' and Randomly Under-Sampled 3DFT Trajectories," Stanford University, p. 1, 2006.

Donoho, "Compressed Sensing," Sep. 14, 2004, pp. 1-34.

Mistretta et al., "Highly constrained backprojection for time-resolved MRI," Abstract, Magnetic Resonance in Medicine, vol. 55, No. 1, Jul. 20, 2005, pp. 30-40.

Schmidt, "Least Squares Optimization with L1-Norm Regularization," Dec. 2005, pp. 1-12.

Lustig et al., "Compressed Sensing MRI," Stanford University, Technical Report No. 2007-3, Jul. 2007, pp. 1-40.

Song et al., "Sparseness prior based iterative image reconstruction for retrospectively gated cardiac micro-CT," Published in final edited form as: Med Phys., vol. 34, No. 11, Nov. 2007, pp. 4476-4483.

O'Halloran et al., "Iterative Projection Reconstruction of Time-Resolved Images Using Highly-Constrained Back-Projection (HYPR)," Magnetic Resonance in Medicine, vol. 59, 2008, pp. 132-139.

* cited by examiner

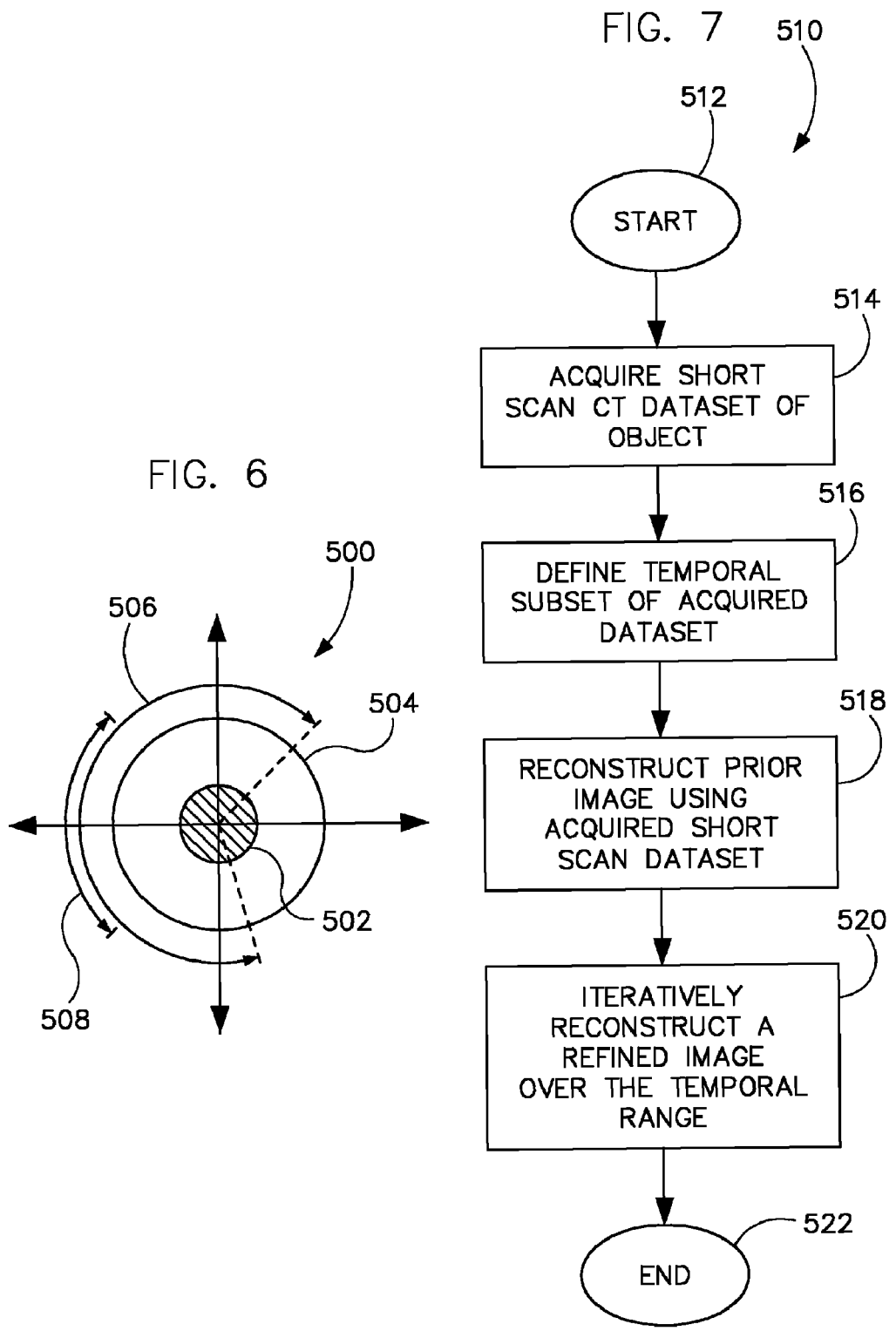

SYSTEM AND METHOD OF PRIOR IMAGE CONSTRAINED IMAGE RECONSTRUCTION USING SHORT SCAN IMAGE DATA AND OBJECTIVE FUNCTION MINIMIZATION

CROSS-REFERENCE TO RELATED APPLICATION

The present application is a continuation of and claims priority to U.S. patent application Ser. No. 12/950,510 filed Nov. 19, 2010, which is a continuation of and claims priority to U.S. patent application Ser. No. 12/775,968 filed May 7, 2010, which claims priority to U.S. Provisional Application 61/314,937 filed Mar. 17, 2010, the disclosures of which are incorporated herein.

BACKGROUND OF THE INVENTION

Embodiments of the invention relate generally to tomographic imaging and, more particularly, to an apparatus and method of acquiring tomographic imaging data and increasing temporal resolution of a tomographic image.

Typically, in x-ray systems, such as a computed tomography (CT) imaging systems, an x-ray source emits a fan-shaped or cone-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam of radiation received at the detector array is typically dependent upon the attenuation of the x-ray beam by the subject. Each detector element of the detector array produces an electrical signal indicative of the attenuated beam received by the detector element. The electrical signals are converted to digital signals and transmitted to a data processing system for analysis, which ultimately produces an image.

Generally, the x-ray source and the detector array are rotated about the gantry within an imaging plane and around the subject. X-ray sources typically include x-ray tubes, which emit the x-ray beam from a focal point. X-ray detectors typically include a collimator for collimating x-ray beams directed toward the detector, a scintillator adjacent to the collimator for converting x-rays to light energy, and photodiodes for receiving the light energy from the scintillator and producing electrical signals therefrom. Typically, each scintillator of a scintillator array converts x-rays to light energy and discharges the light energy to a photodiode adjacent thereto. Each photodiode detects the light energy and generates a corresponding electrical signal. The outputs of the photodiodes are digitized and then transmitted to the data processing system for image reconstruction. The x-ray detector extends typically over a circumferential angular range or fan angle of 60°.

CT imaging encompasses multiple configurations. For example, one configuration includes multi-slice or multi-detector CT imaging (MDCT), which may be employed for cardiac imaging. Such a system may be used to generate a cardiac image using imaging data that is obtained over a portion or phase of a cardiac cycle. Conventionally, the minimum projection angle of imaging data for image reconstruction is 180° of gantry rotation plus the x-ray detector fan angle. Thus, with a typical fan angle of 60°, the minimum projection angle or temporal aperture is 240° of projection data for image reconstruction, and projection data obtained over this "half-scan" or "short scan" range of coverage may be reconstructed using known reconstruction techniques. The amount of time taken to obtain the half-scan projection dataset together with the reconstruction algorithm, in this conventional example, defines the temporal resolution of the imaging system. In other words, the temporal resolution is defined as the time taken to obtain minimally adequate data for image reconstruction and the data actually used in the reconstruction. In this case, short scan data is obtained for 240° of gantry rotation with some type of weighting function, as is understood in the art.

As such, the range of angular coverage (or temporal aperture) and gantry rotational speed are primary factors that define temporal resolution in a MDCT scanner. In a typical single source MDCT scanner, temporal resolution is thus approximately 135 ms for a gantry rotational speed of 270 ms, and approximately 175 ms for a gantry rotational speed of 350 ms with a Parker weighting, as examples. In many imaging applications, such temporal resolution is adequate to provide images with acceptable motion artifacts.

Due to motion of the heart during the 240° of gantry rotation during which short scan data is obtained, however, the temporal resolution may be inadequate, and images reconstructed with short scan data can suffer from blurring, streaking, or other imaging artifacts. Thus, it is desirable to increase temporal resolution in cardiac imaging applications and in applications in general where imaging artifacts may occur due to object motion. In some applications, it would be desirable to increase the temporal resolution by a factor of up to 2, or even greater, in order to improve images and reduce or eliminate image artifacts.

Temporal resolution could be improved by increasing the gantry speed and thereby decreasing overall acquisition time. As such, artifacts may be reduced or eliminated because acquisition occurs over a smaller time period. Generally, however, weight of the gantry components and other forces acting on the gantry limit the speed at which the gantry can operate, and a reduction in the acquisition time typically includes more powerful x-ray tubes in order to achieve comparable image quality. As is known in the art, though, load on the gantry increases generally as a factor that is squared with respect to gantry rotational speed. Thus there are life, reliability, and performance considerations to take into account, and it is highly nontrivial to maintain stability and functionality of components on the gantry at increased gantry speeds.

Another technique to improve temporal resolution includes a two-tube/two-detector system. In such a system, two tubes operate simultaneously, thus decreasing overall acquisition time and increasing the temporal resolution as compared to a single source system. The cost, however, of two-tube/two-detector CT systems can be prohibitive. In addition, limited space on the gantry prevents the placement of two x-ray tubes and two full-FOV detectors. Thus, the second detector often covers only a fraction of the desired scan FOV. Further, a two-tube/two-detector CT system typically includes significantly more utility resources (i.e., coolant flow, electrical) when compared to a single tube system. Thus, imaging suites containing such systems sometimes need significant and costly upgrades to provide the additional utility supply. And, with an increased number of operational components, reliability of the overall system may be compromised because of the doubling in the number of primary components (i.e., tube, detector, and DAS). Thus, though such a system may improve temporal resolution, the increased temporal resolution comes at the cost of increased initial system expense and cost of ongoing operation, costly suite upgrades, and possibly a reduced system reliability when compared to a single source system.

Further, other imaging modalities such as single photon emission computed tomography (SPECT) and positron emission tomography (PET) also suffer from blurring and other image artifacts due to cardiac or respiratory motions. Such blurring may be caused by inadequate data acquisition during a given acquisition, or may be caused by an inordinate amount of time that may be used in order to obtain tomographic imaging data having reduced blurring and image artifact characteristics.

Thus there is a need for a system and method that minimizes motion blurring in tomographic imaging in a cost-effective and overall efficient manner.

BRIEF DESCRIPTION OF THE INVENTION

Embodiments of the invention are directed to a method and apparatus for acquiring imaging data and reconstructing an image having an improved temporal resolution.

According to an aspect of the invention, a tomographic system includes a gantry having an opening for receiving an object to be scanned, a radiation source, a detector positioned to receive radiation from the source that passes through the object, and a computer. The computer is programmed to acquire a short scan angular range of data of the object, and define a temporal subset of the acquired short scan angular range of data for image reconstruction, the defined temporal subset of the acquired short scan angular range of data comprising approximately half of the angular range of the short scan angular range of data. The computer is further programmed to reconstruct a prior image using the acquired short scan angular range of data, and input an estimated image of the object and the prior image into an objective function and minimize the objective function to reconstruct a refined image using the defined temporal subset of scan data and the prior image.

According to another aspect of the invention, a method of tomographic imaging includes positioning a detector to receive radiation from a heart of a patient, acquiring short scan projection datasets of the heart using the detector, reconstructing a prior image of the heart using the acquired short scan projection datasets, and defining a temporally reduced number of projection datasets from the acquired short scan projection datasets, the temporally reduced number of projection datasets comprising approximately half of an angular range of the acquired short scan projection datasets. The method further includes forming an objective function to utilize the prior image and an image estimate therein, minimizing the objective function, and reconstructing a final image of the heart using output from the minimized objective function.

According to yet another aspect of the invention, a computer readable storage medium having stored thereon a computer program comprising instructions which when executed by a computer cause the computer to acquire a set of short scan projections from a cardiac region of a patient over a short scan angular range, reconstruct a prior image of the cardiac region using the acquired set of short scan projections, use an objective function with the prior image and an image estimate input that is based on a temporally defined subset of the acquired short scan projections, wherein the temporally defined subset of the acquired short scan projections is approximately half of the short scan angular range, and minimize the objective function that results in a refined image of the cardiac region.

These and other advantages and features will be more readily understood from the following detailed description of preferred embodiments of the invention that is provided in connection with the accompanying drawings.

BRIEF DESCRIPTION OF THE DRAWINGS

FIG. 6 is a flowchart illustrating data acquisition in a CT system according to an embodiment of the invention.

FIG. 7 is a flowchart illustrating data acquisition and image reconstruction in a CT system according to an embodiment of the invention.

DETAILED DESCRIPTION

Tomographic imaging devices comprise x-ray systems, magnetic resonance (MR) systems, ultrasound systems, computed tomography (CT) systems, positron emission tomography (PET) systems, ultrasound, nuclear medicine, single photon emission computed tomography (SPECT) systems, and other types of imaging systems. Applications of x-ray sources comprise imaging, medical, security, and industrial inspection applications. Embodiments of the invention herein will be described with respect to tomographic imaging systems that include CT, SPECT, and PET. However, it is to be understood that the embodiments of the invention are generally applicable to any imaging system in which data is reconstructed from a temporal window in which data outside of the temporal reconstruction window may be available and employed to improve image reconstruction and reduce blurring and other artifacts therein.

Figure 1:
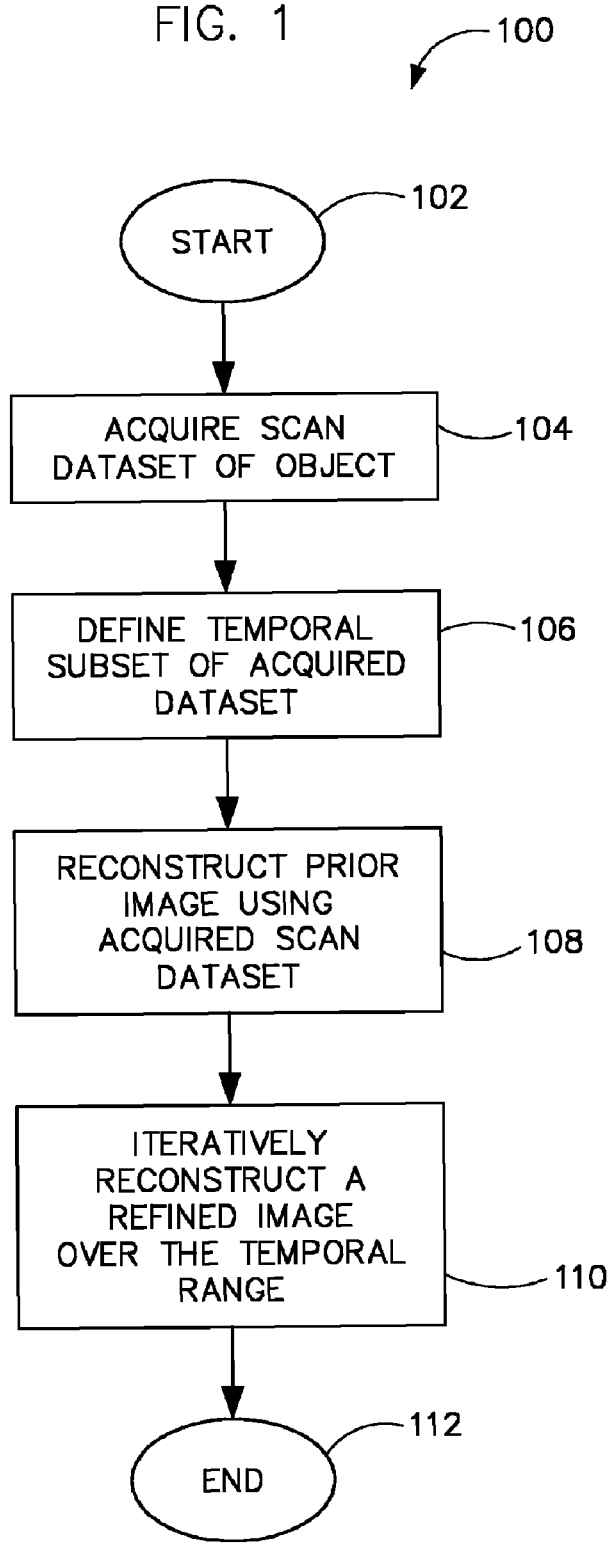
FIG. 1 is a flowchart illustrating data acquisition and image reconstruction according to embodiments of the invention.
Figure 2:
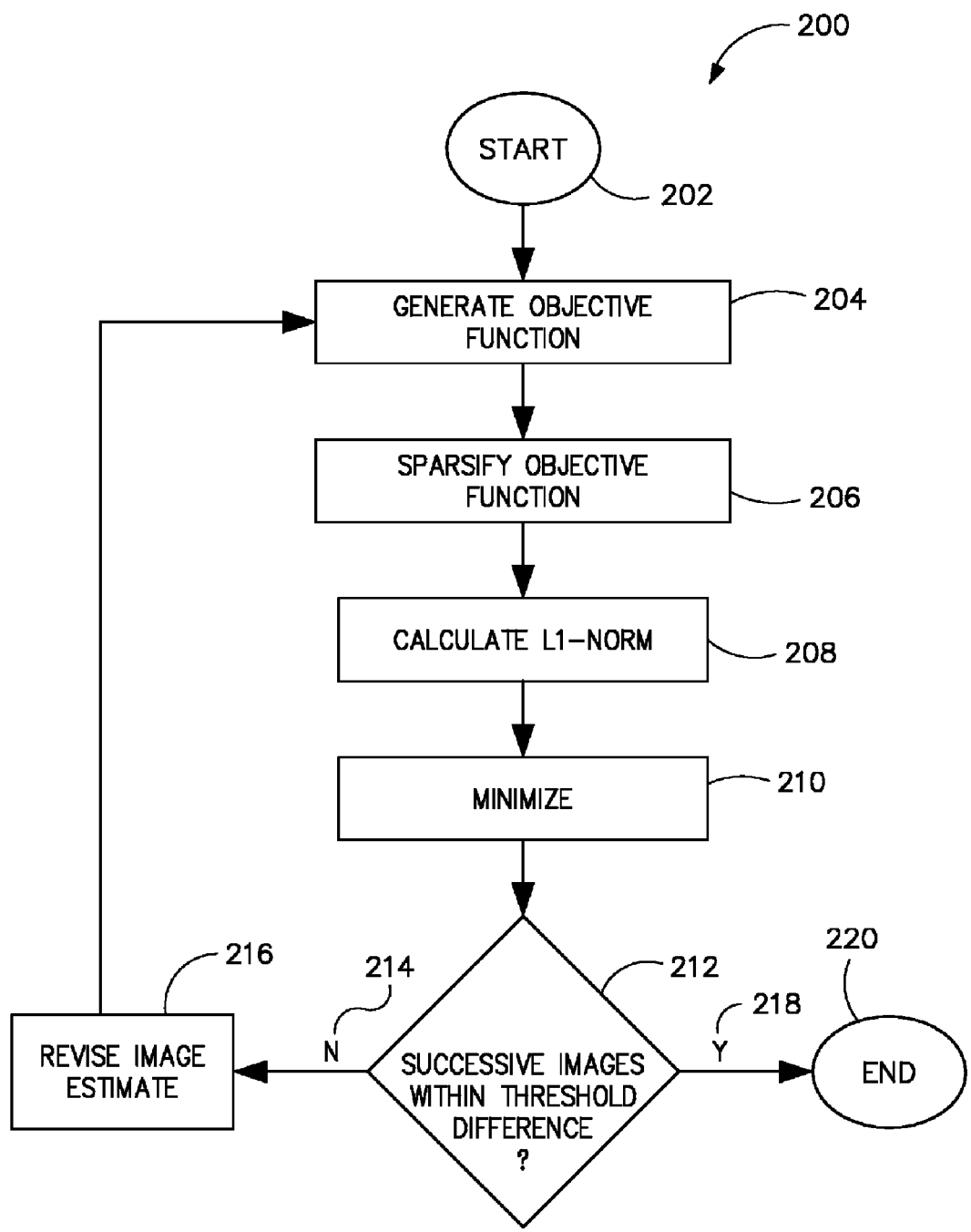
FIG. 2 is a flowchart illustrating aspects of iterative reconstruction of a medical image according to embodiments of the invention.
Figure 3:
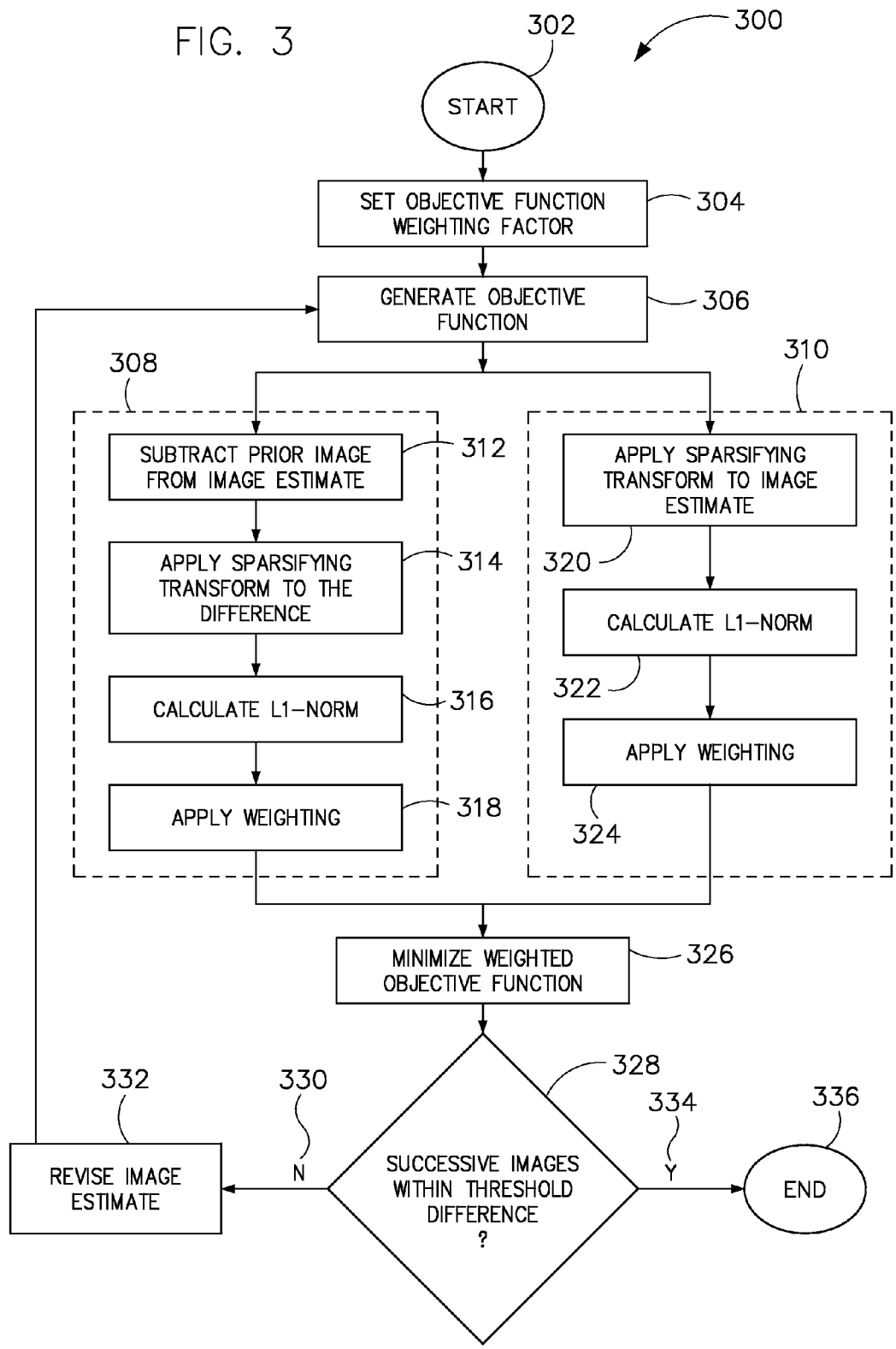
FIG. 3 is a flowchart illustrating aspects of iterative reconstruction of a medical image according to embodiments of the invention.

FIG. 1 is a flowchart general to many tomographic imaging systems illustrating data acquisition and image reconstruction to obtain improved temporal resolution of images according to embodiments of the invention. FIGS. 2 and 3 are flowcharts general to many tomographic imaging systems illustrating image reconstruction according to embodiments of the invention. FIGS. 4-7 illustrate a CT imaging system and a detailed flowchart illustrating data acquisition and image reconstruction to obtain improved temporal resolution of CT images according to embodiments of the invention. Additional imaging modalities and systems, including SPECT (FIGS. 8-9), PET (FIGS. 10-12), and a CT baggage scanner (FIG. 13) incorporating embodiments of the invention will be further described as well.

An enabling technology according to embodiments of the invention is an image reconstruction method referred to as Prior Image Constrained Compressed Sensing (PICCS). Using the method, cardiac tomography images can be accurately reconstructed using projection data acquired over a CT gantry angular range of 90°-130°, and in approximately 120° in one embodiment. As a result and as understood in the art, the temporal resolution of MDCT cardiac imaging can be universally improved by approximately a factor of 2 according to embodiments of the invention, when compared to an image reconstructed using conventional short-scan data acquisition over a 240° angular range.

Cardiac coronary CT imaging can be successfully performed at high heart rates (e.g., up to 94 beats per minute or greater) using a single-source MDCT scanner and projection data from a single heart beat with gantry rotation times of 400 and 350 ms, as examples, according to embodiments of the invention. As will be illustrated, using the PICCS method, temporal resolution of cardiac CT imaging can be effectively improved by approximately a factor of 2 without modifying any scanner hardware versus a traditional method. Thus, embodiments of the invention include a method for single-source MDCT scanners to achieve reliable coronary CT imaging for patients at heart rates higher than the current and conventional heart rate limit of 70 bpm using conventional acquisition and reconstruction techniques. Embodiments of the invention also allow, for instance, a dual-source MDCT scanner to achieve a higher temporal resolution without hardware modifications versus a dual-source MDCT scanner not using embodiments of the invention. Embodiments also allow for improved SPECT and PET temporal resolution as well.

Embodiments of the invention include using half of the acquired short-scan CT data and a low temporal resolution prior image for cardiac reconstruction. As stated, the short-scan angular range is approximately 240°, which is a minimal data sufficiency condition to reconstruct an entire cross section within a scanning field of view. When the cardiac window is narrowed to half of the short-scan window, the available 120° angular range normally does not enable accurate image reconstruction, and the images are contaminated by limited view-angle shading artifacts. Without a priori information, this type of image reconstruction raises classical tomosynthetic reconstruction issues that usually do not have an algorithm to enable accurate image reconstruction.

Embodiments of the invention include incorporation of a prior image, which is reconstructed from the short-scan angular range. Using a prior image having known similarity to a reconstructed target image reduces or eliminates limited-view angle shading artifacts, wherein the prior image does not have limited-view-angle shading artifacts. This constraint is imposed by minimizing a cost or objective function that will be explained later. Two commonly encountered CT sampling issues in x-ray tomographic reconstruction are view angle undersampling and limited-view-angle sampling. In the first case, the angular range of x-ray source trajectory is sufficient to provide accurate reconstruction, but sampling density is too low. In the second case, the angular range is insufficient for accurate reconstruction, as determined by the known Tuy data sufficiency condition. However, when a prior image of the image object is available, the PICCS algorithm may be applied to address the above two issues, which may appear in different clinical applications. Similar issues related to temporal resolution may also be present in imaging applications in other modalities, such as SPECT and PET imaging applications.

According to embodiments of the invention, the PICCS algorithm is used to address the limited-view-angle sampling issue, enabling improved temporal resolution by using CT data from an angular range of about 120° for image reconstruction. According to embodiments of the invention, the prior image is reconstructed using a short-scan angular range of 240°, which is typically 600-700 view angles, while a temporal subset of the short-scan data, used in image reconstruction of approximately 120° includes approximately 300-350 view angles. Because one of the issues being addressed is that of mitigating limited-view angle induced artifacts, embodiments of the invention use the similarity between the prior image and the target image to effectively mitigate the low frequency shading artifacts typically induced by limited-view-angle acquisitions.

The following describes mathematical details of the PICCS algorithm. When a prior image is available, it can then be utilized to significantly sparsify a target image. When a subtraction of the target image I from a prior image $I_P$ is performed, the subtracted image, $I-I_P$ (i.e., a difference image), is significantly more sparse than either $I_P$ or I. When the total number of nonzero image pixels is counted in these three images (I, $I_P$, and the difference image), there are only typically a few thousand pixels (2700 in one example) in the difference image. As understood in the art, this is only approximately 3% of the total pixels in the target image I or the prior image $I_P$. The sparser an image is, the fewer data are needed to accurately reconstruct the image. To enable this image reconstruction, the acquired data should be well distributed in the entire frequency space, although the sampling pattern need not be uniform. When the frequency space is not well sampled as might occur in limited-view-angle sampling, the shading artifacts are still inevitably present in the reconstructed image.

In the PICCS algorithm, the gradient of the difference between the to-be-reconstructed target image, I, and the prior image, $I_P$, is minimized. As such, dissimilarity between the target image I and the prior image $I_P$ is minimized to reduce or eliminate potential limited view-angle shading artifacts in the target image I. This is achieved by minimizing the following objective function:

$$\min[|\nabla_{m,n}(I-I_P)|_{l_1}]; \quad \text{Eqn. 1.}$$

Referring to Eqn. 1, I refers to a target image, and $I_P$ refers to a prior image. However, in coronary computed tomography angiography (CTA) imaging, for example, images reconstructed using Eqn. 1 include significant motion induced streaking artifacts present in the prior image. Thus, the PICCS algorithm includes an additional term, and a total variation of the to-be-reconstructed target image may be included in the above objective function to remove these potential motion streaks. According to the algorithm, the relative weight of these two terms is prescribed by a weighting factor α. In one embodiment weighting factor is α; however, one skilled in the art will recognize that weighting factor α may be selected based on empirical data or historical experience with respect to each imaging modality. As a result, mathematics in the PICCS algorithm includes iteratively solving a constrained minimization problem, as described in the following objective function:

$$\min[\alpha|\nabla_{m,n}(I-I_P)|_{l_1}+(1-\alpha)|\nabla_{m,n}(I)|_{l_1}]; \quad \text{Eqn. 2,}$$

such that PI=Y.

The l 1-norm in the above equations is the sum of the absolute value of each image pixel in an image. P is the system projection operator that calculates the ray sum along a given x-ray path, and Y represents the measured x-ray projection values. The discrete gradient transform in Eqn. 2 is defined as:

$$\nabla_{m,n}I = \sqrt{[I(m+1,n)-I(m,n)]+[I(m,n+1)-I(m,n)]^2};$$  Eqn. 3.

Several methods can be used to solve the constrained minimization problem in Eqn. 2. In one example, Eqn. 2 may be solved in two alternating and iterative steps. In the first step, images may be reconstructed using a commonly known algorithm known as the algebraic reconstruction technique (ART) to meet the constraint PI=Y. Regarding this data constraint condition, the equality is not fulfilled when data contain noise. Thus, a relaxation factor has been introduced in the ART algorithm to account for this inexactness in data consistency constraint. Also regarding the data constraint condition, when the PICCS algorithm is applied to improve temporal resolution, only those projection data from a selected range of view angles corresponding to a target cardiac window are used.

In the second alternating step, the objective function of Eqn. 2 is thus minimized using a known gradient descent method, according to embodiments of the invention. Because the CT projection data set or temporal subset of data is limited to an angular range of about 120°, when the constraint PI=Y is imposed in the ART step, shading artifacts may appear in the ART image, which make it dissimilar from the prior image. Thus, when the objective function of Eqn. 2 is minimized, motion streaks and dissimilarity relative to the prior image will be reduced in the reconstructed image. As such, Eqn. 2 is iteratively solved according to embodiments of the invention, and the process of iterating may be stopped when successively iterated images have a difference that is within a given threshold. In one embodiment the threshold is met when a squared difference of two successively iterated images reaches a predetermined threshold.

Thus, in general and according to embodiments of the invention, and as illustrated in FIG. 1, a technique 100 general to many tomographic imaging systems begins at step 102, and a scan dataset of an object is acquired at step 104 over a given temporal range or during a period that may be particular for the given imaging system. For example, for CT imaging, the data may be obtained during a time for the gantry to acquire short-scan data. For SPECT, the data may be obtained over a period of, for instance, 10 minutes and over 180° of gantry rotation. For PET, imaging data may be obtained over, for example, a 5 minute period. A subset of the acquired data is defined temporally at step 106. In the case of CT, the temporal window for the subset of acquired data ranges from approximately 90° to 130° of gantry rotation and is approximately 120° in one embodiment. For SPECT, a temporally reduced subset of the acquired dataset is defined that includes a fraction of the acquired dataset having a desired temporal distribution. For PET, likewise, a temporally reduced subset of data is defined for image reconstruction.

An image, referred to herein as a prior image, is reconstructed at step 108 using the scan dataset obtained at step 104, and a final or refined image is iteratively reconstructed at step 110 using data from the defined temporal subset of data and using the prior image. The iterative reconstruction includes generating the objective function using an initial image estimate and the prior image, as described above, minimizing the objective function to generate the target image, and iterating if subsequent target images generated are not within a threshold difference, as described above. Technique 100 ends at step 112. Technique 100 may be applied to imaging modalities that include CT, SPECT, and PET. However, it is to be understood that the invention is not to be so limited, and that technique 100 may be applied to any imaging modality in which data is reconstructed from a temporal window in which data outside of the temporal reconstruction window may be available and employed to improve image reconstruction and reducing blurring and other artifacts therein.

FIG. 2 is a flowchart showing image reconstruction occurs according to the technique described above and using an iteration technique. After obtaining imaging data as described above with respect to FIG. 1, iterative reconstruction 200 begins at step 202, and an objective function is generated or formed beginning at step 204 and using an initial image estimate that is refined based on the prior image. In one embodiment, the objective function formed at step 204 is based on Eqn. 1 above. The objective function is sparsified at step 206. In one embodiment, the sparsification at step 206 is via the subtraction of the prior image from the target image. As stated above, such subtraction results in a sparsified image. However, sparsification may also be implemented by applying the discrete gradient transform as described above with respect to Eqn. 3. Thus, sparsification may include subtracting the prior image from the target image, application of the discrete gradient transform, or a combination thereof. Further, it is to be understood that the invention is not limited to the sparsification techniques described, but other sparsification techniques may be applied as commonly understood in the art.

The l 1-norm is calculated at step 208 and, as summarized above, the objective function is minimized at step 210. A final or refined image from the minimization is compared with an image generated previously from an earlier iteration at step 212. If the comparison of successive images is not within the given threshold 214 as described above, then the image estimate is revised at step 216 based on the output from the last minimization, and the objective function is again generated at step 204. However, if successive images are within the given threshold 218, the process ends at step 220. Alternatively, the iterative process can stop after a pre-defined number of iterations.

Referring now to FIG. 3, a flowchart is illustrated showing an image reconstruction technique according another embodiment of the invention. The iterative steps of FIG. 3 are described with respect to the objective function in Eqn. 2. Iterative reconstruction technique 300 begins at step 302, and a weighting factor ($\alpha$ in Eqn. 2) is set at step 304. In one embodiment, $\alpha$ is 0.5. The objective function is generated beginning at step 306, and as seen in Eqn. 2 above, the objective function includes a first term and a second term, the combination of which is minimized as described above. The first term of the objective function corresponds to steps identified in a first box 308, and the second term of the objective function corresponds to steps identified in a second box 310. First box 308 includes, as described above with respect to the first term of Eqn. 2, subtracting a prior image from an image estimate at step 312, sparsifying at step 314 and as described above with respect to FIG. 2, calculating its l 1-norm at step 316, and applying the weighting function $\alpha$ thereto at step 318 as seen in Eqn. 2. Second box 310 includes sparsifying the image estimate at step 320 and as described above with respect to FIG. 2, calculating its l 1-norm at step 322, and applying the weighting function $\alpha$ thereto at step 324 as seen in Eqn. 2. As summarized above, the objective function, including both terms of Eqn. 2 and as generated according to boxes 308, 310 above, is minimized at step 326, and the resulting image from the minimization is compared to an image generated previously and from an earlier iteration at step 328. If the comparison of successive images is not within the given threshold 330 as described above, then the image estimate is revised at step 332 based on the output from the last minimization, and the objective function is again generated at step 306. However, if successive images are within the given threshold 334, the process ends at step 336.

The operating environment of one embodiment of the invention is described with respect to FIGS. 4 and 5, and data acquisition and image reconstruction for a CT application is described below with respect to FIGS. 6 and 7. The CT system is described as a sixty-four-slice CT system. However, it will be appreciated by those skilled in the art that the invention is equally applicable for use with other multi-slice configurations. Moreover, the invention will be described with respect to the detection and conversion of x-rays. One skilled in the art will further appreciate that the invention is equally applicable for the detection and conversion of other high frequency electromagnetic energy. This embodiment of the invention will be described with respect to a "third generation" CT scanner, but is equally applicable with other CT systems.

Figure 4:
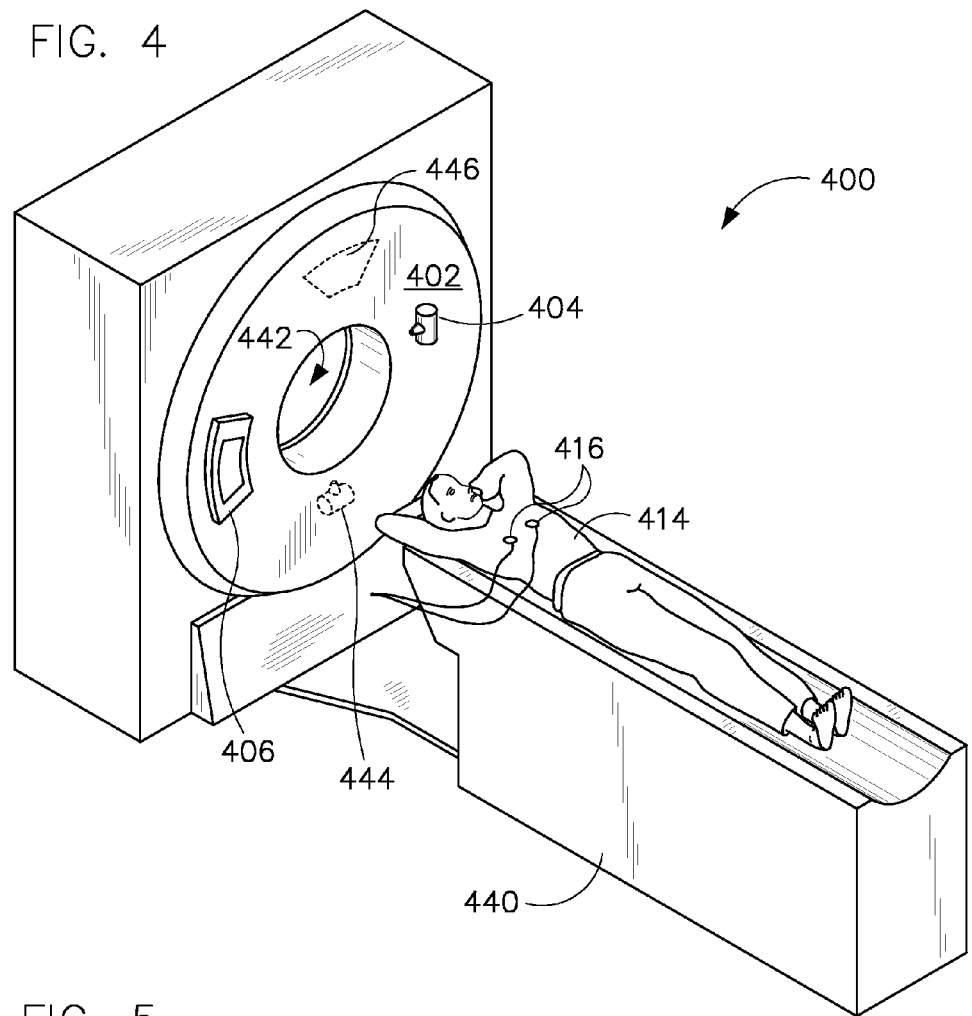
FIG. 4 is a flowchart illustrating data acquisition and image reconstruction in a CT system according to an embodiment of the invention.
Figure 5:
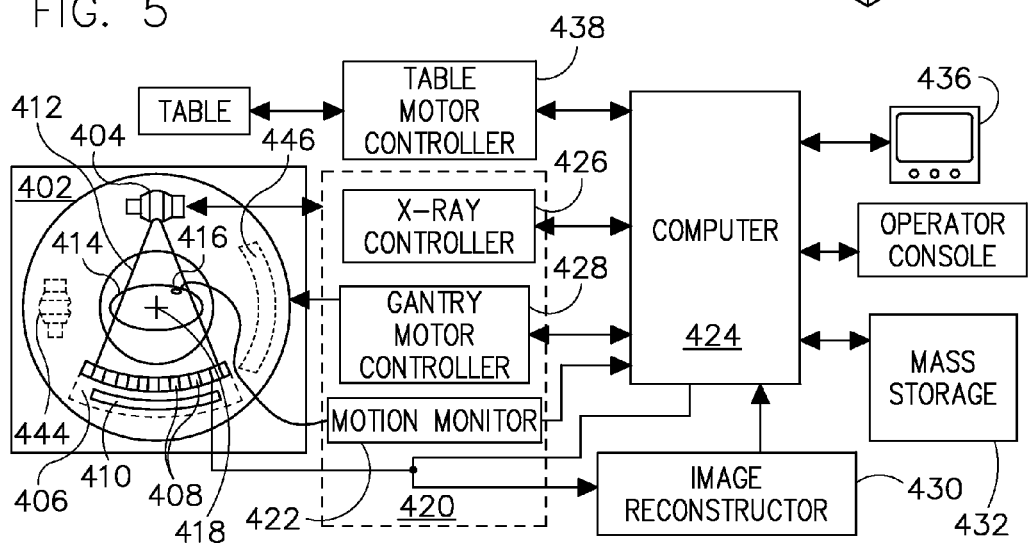
FIG. 5 is a pictorial view of a CT system illustrating aspects of data acquisition as applicable to the flowchart illustrated in FIG. 4.

FIGS. 4 and 5 illustrate, respectively, a pictorial view of a CT system 400 and a schematic block diagram thereof. Referring to FIG. 4, CT imaging system 400 is shown as including a gantry 402 representative of a "third generation" CT scanner. Gantry 402 has an x-ray source 404 that projects a beam of x-rays toward a detector assembly 406 on the opposite side of the gantry 402. Referring now to FIG. 5, detector assembly 406 is formed by a plurality of detectors 408 and a data acquisition systems (DAS) 410. The plurality of detectors 408 sense projected x-rays 412 that pass through a medical patient 414 having, in one embodiment, a motion monitor 416, such as an electrocardiographic device (ECG), is attached thereto. DAS 410 converts data from detectors 408 to digital signals for subsequent processing. Each detector 408 produces an analog electrical signal that represents the intensity of an impinging x-ray beam and hence the attenuated beam as it passes through medical patient 414. During a scan to acquire x-ray projection data, gantry 402 and the components mounted thereon rotate about a center of rotation 418.

Rotation of gantry 402 and operation of x-ray source 404 are governed by a control mechanism 420 of CT imaging system 400. In one embodiment, control mechanism 420 includes a motion monitoring system 422 configured to acquire data from motion monitor 416 and pass patient motion information to a computer 424. Examples of the patient motion information include respiratory and cardiac phase information. Control mechanism 420 includes an x-ray controller 426 that provides power and timing signals to x-ray source 404 and a gantry motor controller 428 that controls a rotational speed and position of gantry 402. An image reconstructor 430 receives sampled and digitized x-ray data from data acquisition systems (DAS) 410 and performs high speed reconstruction. The reconstructed image is applied as an input to computer 424, which stores the image in a mass storage device 432.

Computer 424 also receives commands and scanning parameters from an operator via an operator console 434 that includes an operator interface, such as a keyboard, mouse, voice activated controller, or any other suitable input apparatus. An associated display 436 allows the operator to observe the reconstructed image and other data from computer 424. The operator supplied commands and parameters are used by computer 424 to provide control signals and information to data acquisition systems (DAS) 410, x-ray controller 426 and gantry motor controller 428. In addition, computer 424 operates a table motor controller 438 which controls a motorized table 440 to position medical patient 414 and gantry 402. Particularly, motorized table 440 moves medical patient 414 through a gantry opening 442 of FIG. 4 in whole or in part. In one embodiment, CT imaging system 400 includes a second x-ray source 444 and a corresponding second detector assembly 446 positioned to receive x-rays passing through medical patient 414 in order to obtain additional imaging data. The second source 444/detector 446 combination may be controlled and used to obtain imaging data similarly to that illustrated with respect to x-ray source 404 and detector assembly or collimator 406 and may be used, for instance, to improve the overall temporal resolution of CT imaging system 400 while incorporating embodiments of the invention.

FIGS. 6 and 7 illustrate acquisition and reconstruction of imaging data in a CT system, such as CT imaging system 400 of FIGS. 4 and 5, according to an embodiment of the invention.

Referring now to FIG. 6, a pictorial representation for image acquisition 500 for a CT system, such as CT system 400 in FIGS. 4 and 5, is illustrated. Representation 500 includes an object 502, which may be a heart within a patient, within an inner bore 504 of a CT gantry. Imaging data may be obtained of object 502 over a short-scan angular range 506 or over a portion thereof. In the illustrated embodiment, short-scan angular range 506 is 240°. A temporal subset 508 of the acquired short-scan data may be defined and reconstructed, according to the invention.

Referring now to FIG. 7, a technique 510 begins at step 512 and includes acquiring a short-scan CT dataset at step 514. A temporal subset of data, ranging between 90° and 130°, is defined at step 516, and a prior image is reconstructed of the object using the short-scan data obtained over 240° of gantry rotation at step 518. According to embodiments of the invention, the prior image is reconstructed with conventional means and as understood within the art. In one example, the prior image is reconstructed using a known filtered back-projection (FBP) technique. A final or refined image is iteratively reconstructed at step 520 as described above with respect to FIGS. 2 and 3, and the process ends at step 522 when subsequent images generated are below a given threshold of difference, as understood in the art. In one embodiment the process may be stopped when a squared difference of two successive images reaches a predetermined threshold. Alternatively, the process may stop after a pre-defined number of iterations.

Figure 8:
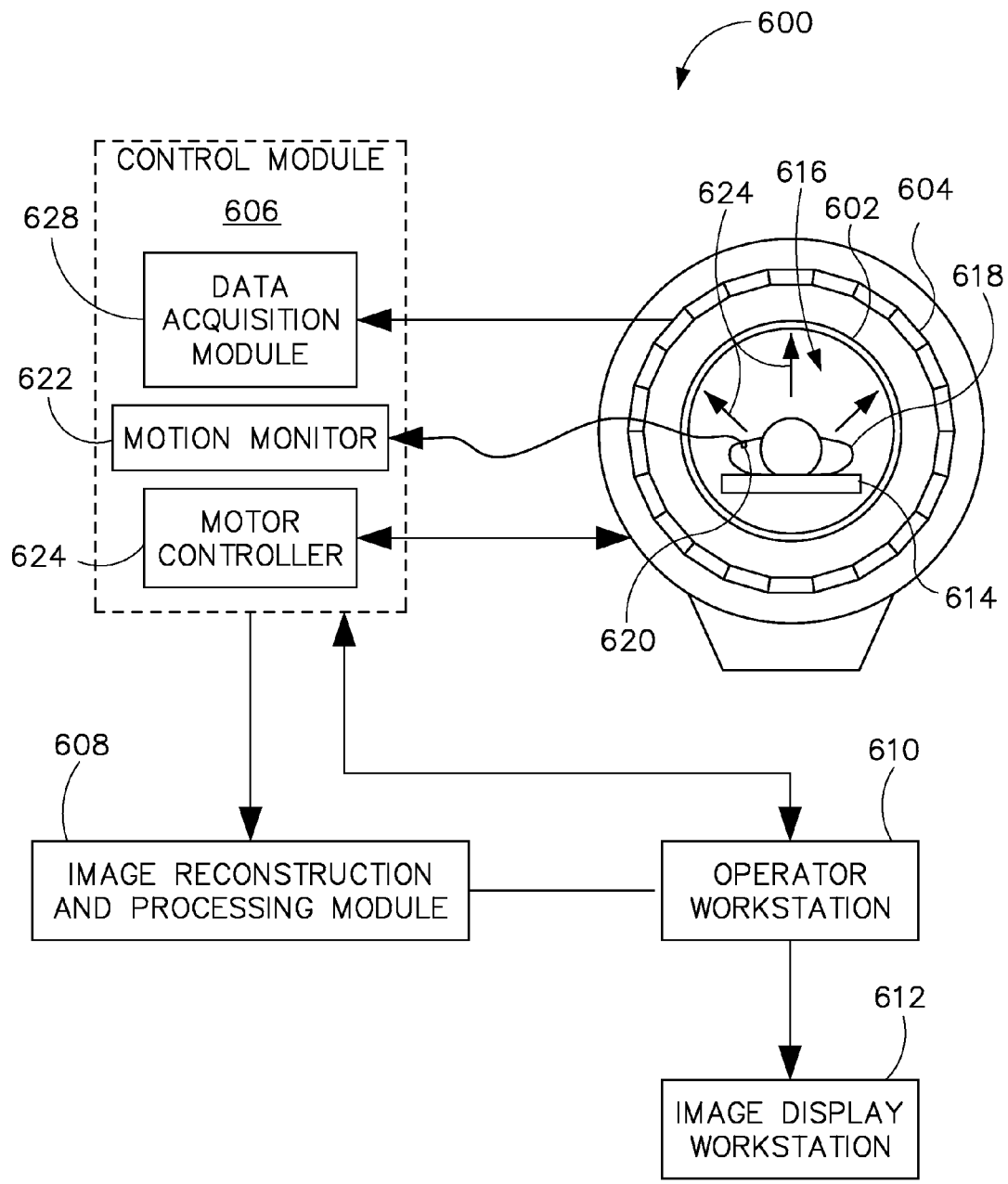
FIG. 8 is a pictorial view of a SPECT imaging system incorporating embodiments of the invention.

FIG. 8 illustrates an exemplary SPECT system 600 for acquiring and processing image data in accordance with embodiments of the invention. SPECT system 600 includes a collimator assembly 602 and a detector assembly 604. SPECT system 600 also includes a control module 606, an image reconstruction and processing module 608, an operator workstation 610, and an image display workstation 612.

As illustrated, a subject support 614 (e.g., a table) may be moved into position in a field-of-view (FOV) 616 of SPECT system 600. In the illustrated embodiment, subject support 614 is configured to support a subject 618 (e.g., a human patient, a small animal, a plant, a porous object, etc.) in position for scanning. Alternatively, subject support 614 may be stationary, while SPECT system 600 may be moved into position around subject 618 for scanning. Subject 618 may be supported in any suitable position for scanning. In one example, subject 618 may be supported in FOV 616 in a generally vertical position, a generally horizontal position, or any other suitable position (e.g., inclined) for the desired scan. In another example, subject 618 may have a motion monitoring system 620, such as an ECG, attached thereto and connected to a motion monitor 622 within control module

606. Thus, motion monitoring system 620 may be controlled and used to obtain patient motion information such as respiratory and cardiac phase information, as examples.

In SPECT imaging, subject 618 is typically injected with a solution that contains a radioactive tracer. The solution is distributed and absorbed throughout subject 618 in different degrees, depending on the tracer employed and, in the case of living subjects, the functioning of the organs and tissues. The radioactive tracer emits electromagnetic rays 624 (e.g., photons or gamma quanta) known as "gamma rays" during a nuclear decay event.

Collimator assembly 602 receives gamma rays 624 emanating from FOV 616. Collimator assembly 602 is generally configured to limit and define a direction and angular divergence of gamma rays 624. In general, collimator assembly 602 is disposed between detector assembly 604 and FOV 616. Gamma rays 624 that pass through collimator assembly 602 impact detector assembly 604. Due to collimation of gamma rays 624 by collimator assembly 602, detection of gamma rays 624 may be used to determine a line of response along which each ray of gamma rays 624 travels before impacting detector assembly 604, allowing localization of an origin for each gamma ray to that line. In general, detector assembly 604 may include a plurality of detector elements configured to detect gamma rays 624 emanating from subject 618 in FOV 616 and passing through one or more apertures defined by collimator assembly 602. In exemplary embodiments, each of the plurality of detector elements in detector assembly 604 produces an electrical signal in response to the impact of the gamma rays 624.

The detector elements may be arranged in detector assembly 604 in any suitable manner. Detector assembly 604 may extend at least partially around FOV 616. In certain embodiments and as illustrated, detector assembly 604 may include modular detector elements arranged around FOV 616. Alternatively, detector assembly 406 may be arranged in a ring that may extend up to 360° around FOV 616. In embodiments, detector assembly 604 may extend from about 180° to about 360° around FOV 616.

To acquire multiple lines of response emanating from subject 618 in FOV 616 during a scan, collimator assembly 602 may be configured to rotate about subject 618 positioned within FOV 616. In one example, collimator assembly 602 may be configured to rotate with respect to detector assembly 604. Detector assembly 604 may be stationary while collimator assembly 602 may be configured to rotate about FOV 616. Alternatively, detector assembly 604 may rotate while collimator assembly 602 is stationary. In another example, collimator assembly 602 and detector assembly 604 may both be configured to rotate, either together or independently of one another. Alternatively, if sufficient pinhole apertures and/or slit apertures are provided through collimator assembly 602 or if the slit apertures are orthogonal to the longitudinal axis of collimator assembly 602, then no rotation may be required.

In the illustrated embodiment, control module 606 includes a motor controller 626 and a data acquisition module 628. In general, gantry motor controller 626 may control a rotational speed and position of collimator assembly 602, detector assembly 604, and/or a position of subject support 614. Data acquisition module 628 may be configured to obtain signals generated in response to impact of gamma rays 624 with detector assembly 604. For example, data acquisition module 628 may receive sampled electrical signals from detector assembly 604 and convert the data to digital signals for subsequent processing by image reconstruction and processing module 608. Any suitable technique for data acquisition may be used with SPECT system 600. In examples and as understood in the art, the data needed for image reconstruction may be acquired in a list or a frame mode. Data may be acquired, parsed, and reconstructed according to embodiments of the invention.

Figure 9:
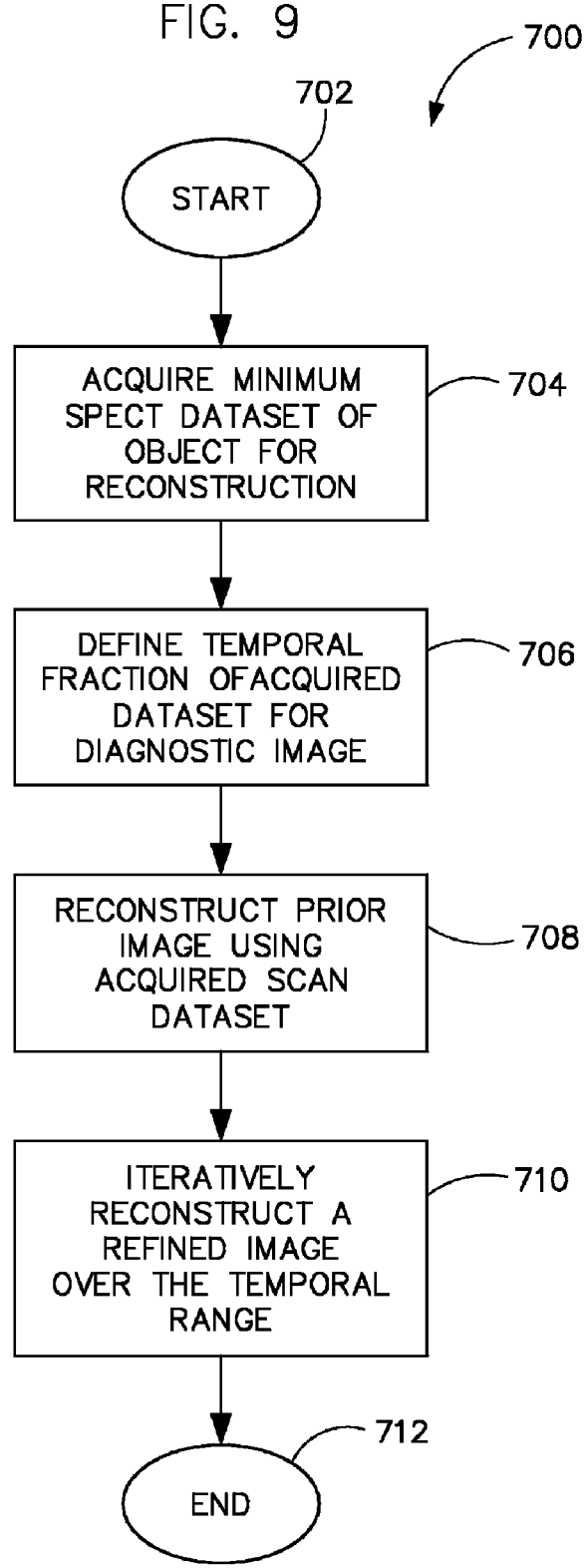
FIG. 9 is a flowchart illustrating data acquisition and image reconstruction in a SPECT system according to an embodiment of the invention.

Referring now to FIG. 9, a flowchart is illustrated showing a technique 700 applying steps of technique 100 to FIG. 1 to a SPECT system to obtain and reconstruct imaging data according to an embodiment of the invention. Technique 700 begins at step 702 and includes acquiring, at step 704, a minimum SPECT dataset of an object such as a heart within patient 618 as illustrated above in FIG. 8. According to embodiments of the invention, gantry speed is relatively slow compared to CT system 400 described above and is in terms of minutes (as opposed to sub-second gantry rotation in typical CT imaging). To improve resolution according to an embodiment of the invention, data is acquired in one embodiment for a 10 minute period and over 180° of rotation, since parallel hole collimation can be used and as understood in the art. Using the concept of iterative reconstruction outlined above as described with respect to FIGS. 2 and 3, only a fraction of the acquired dataset is then used for the final image production. The fraction of the acquired dataset is defined temporally (that is, having using a subset of acquired data having a desired temporal distribution) at step 706, and a prior image is reconstructed at step 708 using the data acquired over the 180° of rotation. The imaging data is iteratively reconstructed at step 710, and the process ends at step 712. Alternatively, the data acquisition can be divided into two steps. In the first step, projections over 180° (for parallel collimation) or 180° (for fan-beam or cone-beam collimator) are quickly collected. Images are reconstructed and serve as the prior images. Note that poor temporal resolution due to slow data acquisition results. Next, a pinhole collimator is used to acquire the projections simultaneously over a limited angular range while the gantry is stationary. Since the projection data are acquired at the same time (without gantry rotation), the data acquisition can be effectively gated by the physiological signals such as ECG. The projections acquired with the pinhole collimator are used for the iterative reconstruction to refine the prior image.

Figure 10:
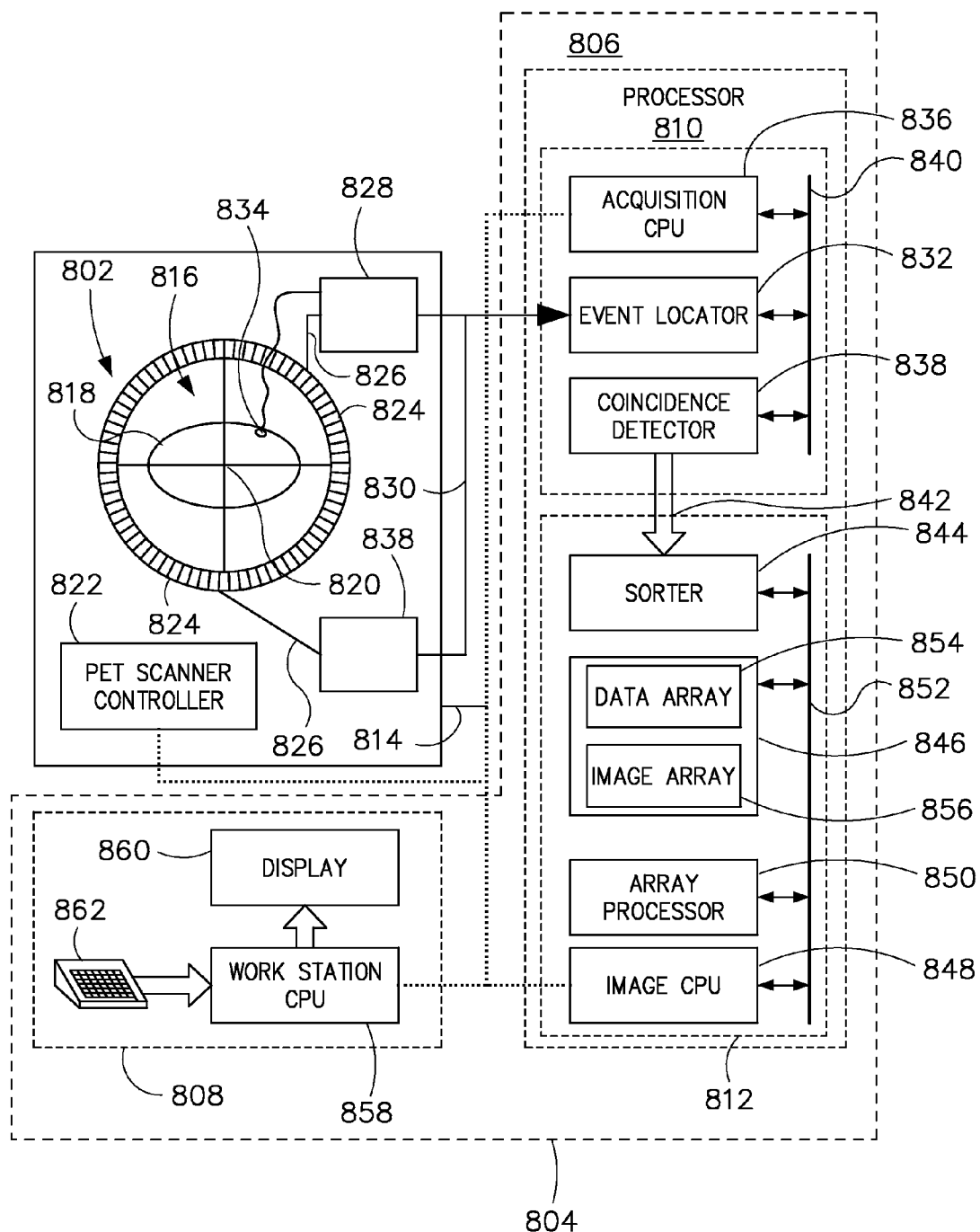
FIG. 10 is a pictorial view and block diagram of a PET system incorporating embodiments of the invention.
Figure 11:
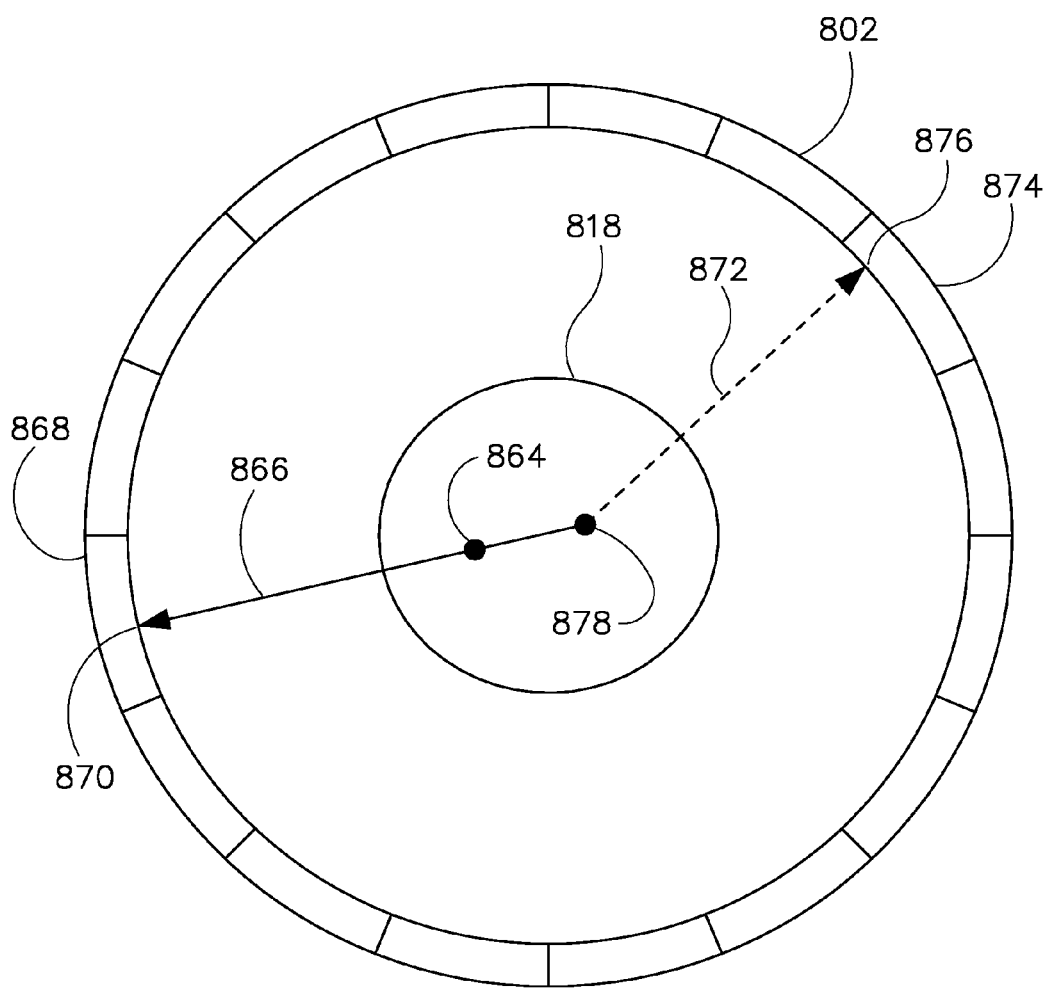
FIG. 11 is a view of a detector ring of the PET system of FIG. 10.

FIG. 10 is a block diagram of an exemplary embodiment of a PET system 800 in which various embodiments of the invention may be implemented. PET system 800 includes a plurality of detector ring assemblies. One such detector ring assembly, detector ring assembly 802, is illustrated in FIG. 11. PET system 800 further includes a controller 804 to control normalization and image reconstruction processes. Controller 804 includes a processor 806 and an operator workstation 808. Processor 806 includes a data acquisition processor 810 and an image reconstruction processor 812 that are interconnected and connected with detector ring assembly 802 via a communication link 814. PET system 800 acquires scan data and transmits the data to data acquisition processor 810. The scanning operation is controlled from operator workstation 808. The data acquired by data acquisition processor 810 is reconstructed using image reconstruction processor 812.

Detector ring assembly 802 includes a central opening 816 in which a patient or object 818 may be positioned using, for example, a motorized table (not shown) that is aligned with a central axis 820 of detector ring assembly 802. The motorized table moves object 818 into central opening 816 of detector ring assembly 802 in response to one or more commands received from operator workstation 808. A PET scanner controller 822, also referred to as the gantry controller, is provided (e.g., mounted) within PET system 800. PET scanner controller 822 responds to commands received from operator workstation 808 through communication link 814.

Detector ring assembly 802 includes a plurality of detector units 824 (e.g., in one known PET system, there are 420 crystals per ring, and 24 rings in the scanner). While not shown, it is contemplated that each detector unit 824 includes a set of scintillator crystals arranged in a matrix disposed in front of a plurality of photomultiplier tubes (e.g., four tubes). When a photon collides with a scintillator crystal on a detector unit 824, it produces a scintilla on the scintillator crystal. Each photomultiplier tube produces an analog signal on a communication line 826 when a scintillation event occurs. A set of acquisition circuits 828 is provided to receive these analog signals. Acquisition circuits 828 produce digital signals indicating a location in 3-dimensional (3D) space and a total energy of the event. Acquisition circuits 828 also produce an event detection pulse, which indicates the time or moment the scintillation event occurred. These digital signals are transmitted through a communication link 830 such as a cable, for example, to an event locator circuit 832 in data acquisition processor 810. In one embodiment, PET system 800 includes a motion monitoring system 834, such as an ECG, attached to object 818 and attached to acquisition circuit 828 that may be used to obtain patient motion information such as respiratory and cardiac phase information, as examples, via data acquisition processor 810.

Data acquisition processor 810 includes event locator circuit 832, an acquisition CPU 836 and a coincidence detector 838. Data acquisition processor 810 periodically samples the signals produced by acquisition circuits 828. Acquisition CPU 836 controls communications on a back-plane bus 840 and on communication link 814. Event locator circuit 832 processes information regarding each valid event and provides a set of digital numbers or values indicative of the detected event. For example, this information indicates when the event took place and the position of the scintillation crystal that detected the event. An event data packet (not shown) containing the event information is communicated to coincidence detector 838 through back-plane bus 840. Coincidence detector 838 receives the event data packets from event locator circuit 832 and determines if any two of the detected events are in coincidence. Coincidence is determined by a number of factors. First, time markers in each event data packet should be within a predetermined time period of each other such as, for example, 12.5 nanoseconds. Second, a line of response (LOR) formed by a straight line joining the two detectors that detect the coincidence event should pass through the central opening 816 or through a field of view in PET system 800. Events that cannot be paired are discarded. Coincident event pairs are located and recorded as a coincidence data packet that is communicated through a communication link 842 to a sorter 844 in image reconstruction processor 812.

Image reconstruction processor 812 includes sorter 844, a memory module 846, an image CPU 848, an array processor 850 and a back-plane bus 852. Sorter 844 counts all events occurring along each projection ray and organizes them into 3D data. This 3D data (or sinograms) is organized, in one exemplary embodiment, as a data array 854. Data array 854 is stored in memory module 846. Back-plane bus 852 is linked to communication link 814 through image CPU 848, and image CPU 848 controls communication through back-plane bus 852. Array processor 850 is also connected to back-plane bus 852. Array processor 850 receives data array 854 as an input and reconstructs images in the form of image arrays 856. Resulting image arrays 856 are stored in memory module 846.

Images stored in image arrays 856 are communicated by image CPU 848 to operator workstation 808. Operator workstation 808 includes a CPU 858, a display device 860 and an input device 862. Acquisition CPU 858 connects to communication link 814 and receives inputs (e.g., user commands) from input device 862. Input device 862 may be, for example, a keyboard, mouse, or a touch-screen panel. Through input device 862 and associated control panel switches, an operator can control calibration of PET system 800 and can control positioning of object 818 for a scan. Similarly, an operator can control display of a resulting image on display device 860 and perform image-enhancement functions using programs executed by acquisition CPU 858.

The data array received by array processor 850 may be corrected for errors before being reconstructed. The level of correction may be based on, for example, a desired or required resolution level for a reconstructed image. One correction includes removing scatter coincidences from the image data.

FIG. 11 illustrates a single scatter coincidence with respect to detector ring assembly 802 of FIG. 10. An annihilation event occurs at an annihilation point 864 inside object 818. The annihilation event produces a photon 866 that impacts a detector element 868 at a first detection point 870, and a scattered photon 872 that impacts a detector element 874 at a second detection point 876. Scattered photon 872 is scattered from a scattering point 878 inside object 818. Detector element 868 records a time at which photon 866 is detected and a time at which scattered photon 872 is detected. Detector element 868 and detector element 874 form a detector pair. As known in the art, detector element pair 868/874 map to a unique sinogram bin with indices, r and $\theta$, and indices r and $\theta$ denote a radial distance from the center of the detector ring and an angle of the line joining 868 and 876 from a horizontal axis, respectively. A difference between detection times for first detection point 870 and second detection point 876 maps to a unique time bin index for the time-of-flight scatter sinogram. For each of the plurality of detector pairs, the total number of annihilation events and the time at which each event is recorded is sent to processor 806 (shown in FIG. 11). Based on the received information, the detected events are binned into sinograms with indices r and $\theta$, used to generate a time-of-flight scatter sinogram $S(r, \theta, t)$.

Figure 12:
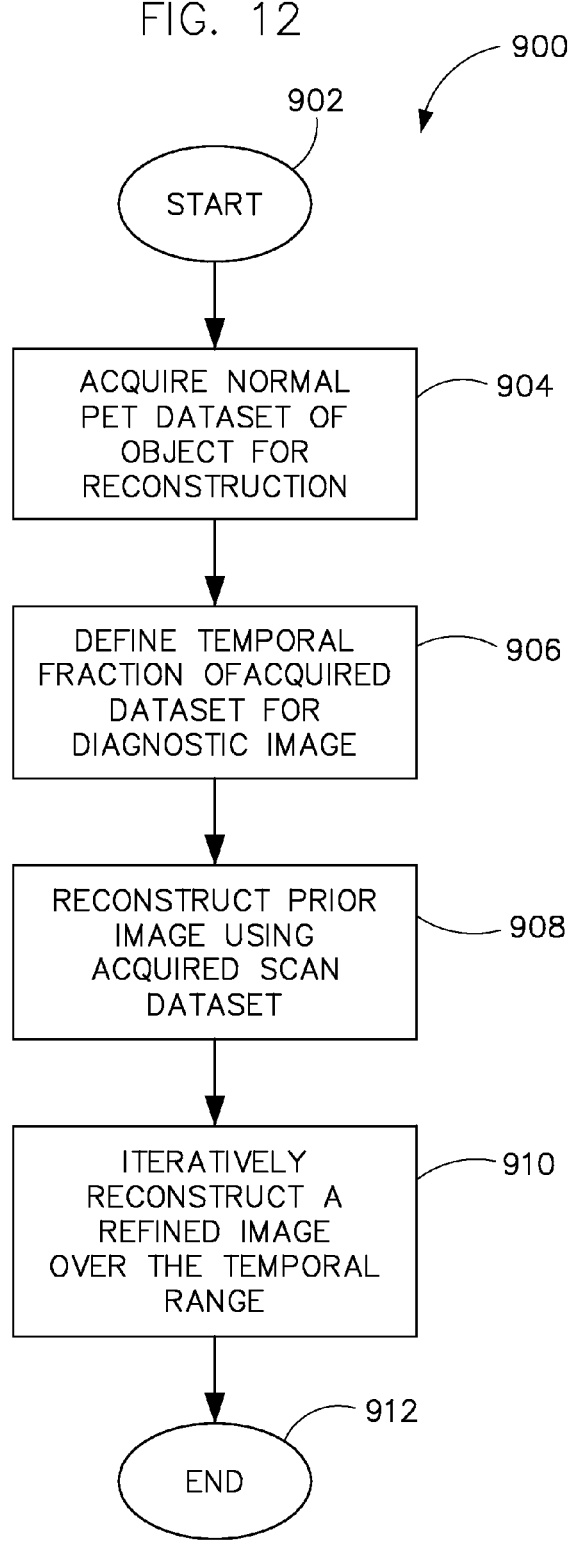
FIG. 12 is a flowchart illustrating data acquisition and image reconstruction in a PET system according to an embodiment of the invention.

Referring now to FIG. 12, imaging data is obtained and reconstructed using the PET system illustrated with respect to FIGS. 10 and 11 and according to technique 100 described with respect to FIG. 1 above. Technique 900 begins at step 902 includes acquiring at step 904 a PET dataset of an object, such as a heart within patient or object 818 as illustrated above in FIG. 10. According to the invention, a conventional PET dataset may be obtained (e.g., over a 5 minute period) and used to generate the prior image, and reconstructed according to the invention. Data collected over a fractional period of time (i.e., a defined temporal window) may then be used to refine the prior image to remove motion monitoring system 834 of FIG. 10, a quiescent time period may be selected within the original acquisition window (5 minutes, in this example) to iteratively produce a final or refined image. Thus, the final image exhibits the noise property of the longer scan time (e.g., 5 minutes) but exhibits the motion property of an improved temporal window. As such, and as described, a conventional or normal PET dataset is obtained of the object at step 904. A fraction of the acquired dataset is defined temporally at step 906, a prior image is reconstructed using the dataset obtained at step 908, and an image is iteratively reconstructed as describe above at step 910 with respect to FIGS. 2 and 3. The process ends at step 912.

Figure 13:
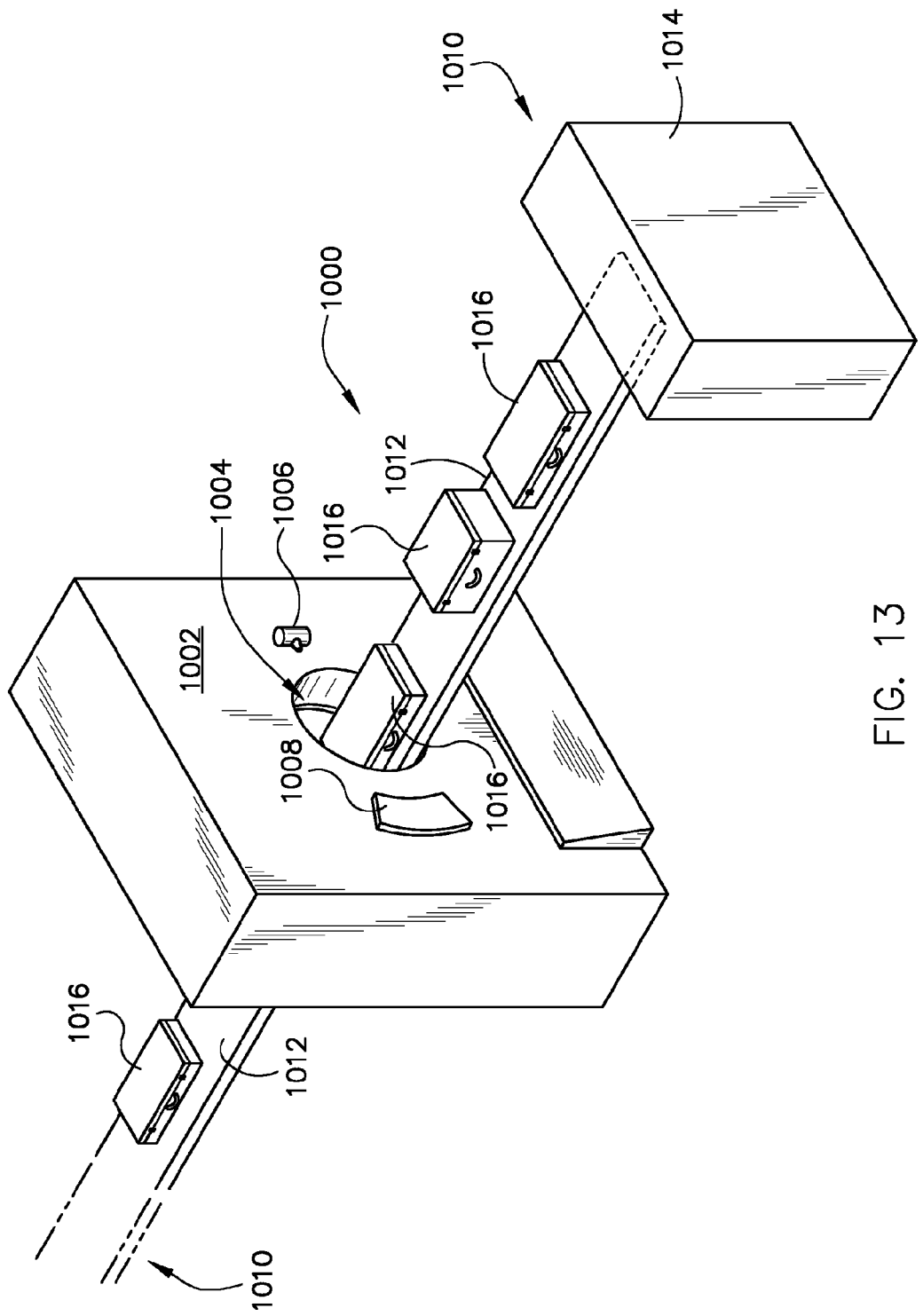
FIG. 13 is a pictorial view of a baggage scanning system incorporating embodiments of the invention.

Referring now to FIG. 13, there is shown a package/baggage inspection system 1000 that can use the image acquisition and reconstructions techniques according to embodiments of the invention and which includes a rotatable gantry 1002 having an opening 1004 therein through which packages or pieces of baggage may pass. The rotatable gantry 1002 houses one or more x-ray energy sources 1006 as well as a detector assembly 1008 having scintillator arrays comprised of scintillator cells. A conveyor system 1010 is also provided and includes a conveyor belt 1012 supported by structure 1014 to automatically and continuously pass packages or baggage pieces 1016 through opening 1004 to be scanned. Objects 1016 are passed through opening 1004 by conveyor belt 1012, imaging data is then acquired, and the conveyor belt 1012 removes the packages 1016 from opening 1004 in a controlled and continuous manner. As a result, postal inspectors, baggage handlers, and other security personnel may non-invasively inspect the contents of packages 1016 for explosives, knives, guns, contraband, etc.

An implementation of embodiments of the invention in an example comprises a plurality of components such as one or more of electronic components, hardware components, and/or computer software components. A number of such components can be combined or divided in an implementation of the embodiments of the invention. An exemplary component of an implementation of the embodiments of the invention employs and/or comprises a set and/or series of computer instructions written in or implemented with any of a number of programming languages, as will be appreciated by those skilled in the art.

An implementation of the embodiments of the invention in an example employs one or more computer readable storage media. An example of a computer-readable signal-bearing medium for an implementation of the embodiments of the invention comprises the recordable data storage medium of the image reconstructor 34, and/or the mass storage device 38 of the computer 36. A computer-readable storage medium for an implementation of the embodiments of the invention in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory.

A technical contribution for the disclosed method and apparatus is that it provides for a computer-implemented apparatus and method of tomographic imaging and, more particularly, an apparatus and method of acquiring tomographic imaging data and increasing temporal resolution of a tomographic image.

According to an aspect of the invention, a tomographic system includes a gantry having an opening for receiving an object to be scanned, a radiation source, a detector positioned to receive radiation from the source that passes through the object, and a computer. The computer is programmed to acquire a short scan angular range of data of the object, and define a temporal subset of the acquired short scan angular range of data for image reconstruction, the defined temporal subset of the acquired short scan angular range of data comprising approximately half of the angular range of the short scan angular range of data. The computer is further programmed to reconstruct a prior image using the acquired short scan angular range of data, and input an estimated image of the object and the prior image into an objective function and minimize the objective function to reconstruct a refined image using the defined temporal subset of scan data and the prior image.

According to another aspect of the invention, a method of tomographic imaging includes positioning a detector to receive radiation from a heart of a patient, acquiring short scan projection datasets of the heart using the detector, reconstructing a prior image of the heart using the acquired short scan projection datasets, and defining a temporally reduced number of projection datasets from the acquired short scan projection datasets, the temporally reduced number of projection datasets comprising approximately half of an angular range of the acquired short scan projection datasets. The method further includes forming an objective function to utilize the prior image and an image estimate therein, minimizing the objective function, and reconstructing a final image of the heart using output from the minimized objective function.

According to yet another aspect of the invention, a computer readable storage medium having stored thereon a computer program comprising instructions which when executed by a computer cause the computer to acquire a set of short scan projections from a cardiac region of a patient over a short scan angular range, reconstruct a prior image of the cardiac region using the acquired set of short scan projections, use an objective function with the prior image and an image estimate input that is based on a temporally defined subset of the acquired short scan projections, wherein the temporally defined subset of the acquired short scan projections is approximately half of the short scan angular range, and minimize the objective function that results in a refined image of the cardiac region.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A computerized tomographic system configured to:
   acquire short scan data of an object within a single revolution of a detector array about the object over a first angular range of rotation of the detector array about the object;
   define a temporal subset of the acquired short scan data over a second angular range of rotation of the detector that is less than the first angular range of rotation;
   generate a mathematical function that is based on the acquired short scan data and the defined temporal subset of data;
   minimize the mathematical function; and
   generate an image of the object using the minimized mathematical function and the data acquired over the second angular range of rotation of the detector.

2. The computerized tomographic system of claim 1 wherein the short scan data is defined as 180° of gantry rotation plus an x-ray detector fan angle.

3. The computerized tomographic system of claim 2 wherein the x-ray detector fan angle is approximately 60°.

4. The computerized tomographic system of claim 1 wherein the second angular range of rotation ranges from approximately 90° to 130° of gantry rotation.

5. The computerized tomographic system of claim 1 wherein the second angular range of rotation is approximately 120° of gantry rotation.

6. The computerized tomographic system of claim 1 wherein the second angular range of rotation falls within the first angular range of rotation.

7. The computerized tomographic system of claim 1 wherein the short scan data of the object includes approximately 600-700 view angles of data.

8. The computerized tomographic system of claim 1 wherein the temporal subset of acquired short scan data includes approximately 300-350 view angles of data.

9. The computerized tomographic system of claim 1 wherein the mathematical function includes subtraction of a prior image from an image estimate, wherein the prior image is generated from the acquired short scan data, and the image estimate is formed using the defined temporal subset of data.

10. The computerized tomographic system of claim 9 wherein the prior image is generated using a filtered back-projection (FBP) technique.

11. The computerized tomographic system of claim 1 wherein a prior image is formed using the acquired short scan data, an image estimate is formed using the temporal subset of data, the prior image is used to sparsify the image estimate, and the sparsified image is used in the mathematical function.

12. The computerized tomographic system of claim 11 wherein the prior image is used to sparsify the image estimate by calculating a difference between the prior image and the image estimate.

13. The computerized tomographic system of claim 9 wherein the system is configured to iterate to generate the image by being caused to:
generate a resulting image from the minimized mathematical function;
compare the resulting image to the image estimate;
re-generate the mathematical function based on the prior image and the resulting image; and
minimize the re-generated mathematical function.

14. The computerized tomographic system of claim 13 wherein, in comparing the resulting image to the image estimate, if a difference between the resulting image and the image estimate is within a given threshold, then stop iterating.

15. The computerized tomographic system of claim 13 wherein, in comparing the resulting image to the image estimate, if a squared difference between the resulting image and the image estimate is within a given threshold, then stop iterating.

16. The computerized tomographic system of claim 9 comprising sparsifying the mathematical function using a discrete gradient transform.

17. The computerized tomographic system of claim 1 wherein the second angular range of rotation is approximately half that of the first angular range of rotation.

18. A method of tomographic imaging comprising:
acquiring short scan projection datasets of a heart using a detector;
defining a temporally reduced subset of the short scan projection datasets;
forming a mathematical function based on the short scan projection datasets and based on the temporally reduced subset of datasets;
minimizing the mathematical function; and
generating an image of the heart using an output of the minimized mathematical function.

19. The method of claim 18 comprising:
generating a prior image based on the acquired short scan projection datasets;
generating an image estimate based on the temporally reduced subset of scan projection datasets; and
forming the mathematical function using the prior image and the image estimate.

20. The method claim 19 wherein forming the mathematical function includes subtracting the prior image from the image estimate, the method further comprising:
generating a resulting image as a result of minimizing the mathematical function;
comparing a difference between the resulting image and the image estimate, and if the difference is greater than a threshold value, then;
re-generating the image estimate based on the resulting image;
re-forming the mathematical function based on the re-generated image estimate and based on the prior image; and
minimizing the re-formed mathematical function.

21. A computerized readable storage medium having stored thereon a computer program comprising instructions which when executed by a computer cause the computer to:
acquire half scan data of a heart during a single revolution of a detector array about the heart;
define a temporal aperture as a portion of a rotation of the detector array about the heart that is less than an angular range of rotation during which the half scan data is acquired;
generate a cost function that is based on the half scan data and based on data acquired during the temporal aperture;
minimize the cost function; and
generate an image of the object using the minimized cost function to constrain an image formed using data acquired in the temporal aperture.

22. The computerized tomographic system of claim 21 wherein the cost function includes subtraction of a prior image from an image estimate, wherein the prior image is generated from the half scan data, and the image estimate is formed using the data acquired during the temporal aperture.

23. The computerized tomographic system of claim 22 wherein the cost function is:

$$\min[\alpha|\nabla_{m,n}(I-I_p)|_{l_1}+(1-\alpha)|\nabla_{m,n}(I)|_{l_1}];$$

wherein the mathematical function includes iteratively solving a constrained minimization problem defined as PI=Y, wherein l 1-norm in is a sum of an absolute value of each image pixel in an image, P is a system projection operator that calculates a ray sum along a given x-ray path, Y represents measured x-ray projection values, I is the image estimate, and $I_p$ is the prior image.

24. The computerized tomographic system of claim 23 wherein $\nabla_{m,n}(I)$ is a discrete gradient transform defined as:

$$\nabla_{m,n}(I)=\sqrt{[I(m+1,n)-I(m,n)]^2+[I(m,n+1)-I(m,n)]^2}.$$

25. The computerized tomographic system of claim 22 wherein the system is configured to iterate to generate the image by being caused to:
generate a resulting image from the minimized cost function;
compare the resulting image to the image estimate, if a difference between the resulting image and the image estimate is not within a given threshold, then:
re-generate the cost function based on the prior image and the resulting image; and
minimize the re-generated cost function.

26. An imaging system configured to:
acquire short scan data of an object;
define a temporal subset of the acquired short scan data;

form a prior image using the acquired short scan data;
form a target image using the defined temporal subset of data, wherein formation of the target image is constrained by the prior image.

27. The imaging system of claim 26 wherein the short scan data is acquired within a single revolution of a detector array about the object.

28. The imaging system of claim 26 wherein the imaging system is a computed tomography (CT) system.

29. The imaging system of claim 26 wherein the imaging system is configured to:
generate a mathematical function that is based on the prior image and an image estimate;
minimize the mathematical function; and
form the target image using the minimized mathematical function.

30. The imaging system of claim 26 wherein:
the short scan data is acquired over a first angular range of rotation of the detector array about the object; and
the temporal subset of data is defined over a second angular range of rotation of the detector that is less than the first angular range of rotation.

31. The imaging system of claim 30 wherein the second angular range of rotation occurs within the first angular range of rotation.

* * * * *

UNITED STATES PATENT AND TRADEMARK OFFICE
CERTIFICATE OF CORRECTION

PATENT NO. : 8,315,353 B1  
APPLICATION NO. : 13/493051  
DATED : November 20, 2012  
INVENTOR(S) : Hsieh et al.

Page 1 of 1

It is certified that error appears in the above-identified patent and that said Letters Patent is hereby corrected as shown below:

Col. 18, line 42 (Claim 23), delete $$\text{``}\min[\alpha|\nabla_{m,n}(I-I_p)|_{l_1} + (1-\alpha)|\nabla_{m,n}(I)|_{l_1}];\text{''}$$

and substitute therefore $$\text{--}\min[\alpha|\nabla_{m,n}(I-I_p)|_{\ell_1} + (1-\alpha)|\nabla_{m,n}(I)|_{\ell_1}];\text{--; and}$$

Col. 18, line 45 (Claim 23), delete "wherein l 1-norm" and
substitute therefore -- wherein $\ell_1$-norm --.

Signed and Sealed this
Fifth Day of February, 2013

Teresa Stanek Rea
*Acting Director of the United States Patent and Trademark Office*